(12) United States Patent
Swoboda

(10) Patent No.: US 12,178,894 B2
(45) Date of Patent: Dec. 31, 2024

(54) BIO-BASED THICKENING COMPOSITION COMPRISING A POLY(FARNESENE)

(71) Applicant: TOTALENERGIES ONETECH, Courbevoie (FR)

(72) Inventor: Benjamin Swoboda, Orgeval (FR)

(73) Assignee: TOTALENERGIES ONETECH, Courbevoie (FR)

( * ) Notice: Subject to any disclaimer, the term of this patent is extended or adjusted under 35 U.S.C. 154(b) by 670 days.

(21) Appl. No.: 17/419,183

(22) PCT Filed: Jan. 10, 2020

(86) PCT No.: PCT/FR2020/050031
§ 371 (c)(1),
(2) Date: Jun. 28, 2021

(87) PCT Pub. No.: WO2020/144440
PCT Pub. Date: Jul. 16, 2020

(65) Prior Publication Data
US 2022/0110840 A1    Apr. 14, 2022

(30) Foreign Application Priority Data

Jan. 10, 2019   (FR) ...................................... 1900252

(51) Int. Cl.
| | | |
|---|---|---|
| A61K 8/04 | (2006.01) | |
| A61K 8/81 | (2006.01) | |
| A61K 8/92 | (2006.01) | |
| A61Q 17/04 | (2006.01) | |
| A61Q 19/00 | (2006.01) | |

(52) U.S. Cl.
CPC ............ *A61K 8/042* (2013.01); *A61K 8/8111* (2013.01); *A61K 8/922* (2013.01); *A61Q 17/04* (2013.01); *A61Q 19/00* (2013.01); *A61K 2800/48* (2013.01)

(58) Field of Classification Search
CPC ...... A61K 8/042; A61K 8/8111; A61K 8/922; A61K 2800/48; A61K 8/31; A61K 8/062; A61K 8/92; A61Q 17/04; A61Q 19/00
See application file for complete search history.

(56) References Cited

U.S. PATENT DOCUMENTS

| | | |
|---|---|---|
| 9,334,394 B1 | 5/2016 | Henning et al. |
| 2006/0264684 A1 | 11/2006 | Petri et al. |
| 2009/0300970 A1 | 12/2009 | Perego et al. |
| 2012/0010370 A1* | 1/2012 | McPhee ................ C08L 51/003 525/332.1 |
| 2013/0251846 A1* | 9/2013 | Mo .......................... A23G 4/06 426/3 |
| 2015/0051332 A1 | 2/2015 | Koda et al. |
| 2015/0353841 A1 | 12/2015 | Rispoli et al. |
| 2018/0072826 A1 | 3/2018 | Henning et al. |
| 2018/0140656 A1 | 5/2018 | Germanaud et al. |
| 2020/0054546 A1 | 2/2020 | Swoboda et al. |

FOREIGN PATENT DOCUMENTS

| | | |
|---|---|---|
| EP | 2368967 | 9/2011 |
| JP | 2015221772 A * | 12/2015 |
| WO | 2018029143 | 2/2018 |

OTHER PUBLICATIONS

JP-2015221772-A translated (Year: 2015).*

* cited by examiner

*Primary Examiner* — Robert A Wax
*Assistant Examiner* — John Seungjai Kwon
(74) *Attorney, Agent, or Firm* — DUANE MORRIS LLP; Gregory M. Lefkowitz; Brandon A. Chan

(57) ABSTRACT

The invention relates to a thickening composition intended for topical application on the skin, lips or skin appendages, said thickening composition comprising at least one oil derived from a biological source and at least one poly (farnesene) polymer having a number average molar mass ranging from 10,000 to 120,000 g/mol. The invention also relates to a cosmetic composition comprising the thickening composition according to the invention and the use of the thickening composition according to the invention in a cosmetic composition.

18 Claims, No Drawings

BIO-BASED THICKENING COMPOSITION COMPRISING A POLY(FARNESENE)

CROSS-REFERENCE TO RELATED APPLICATIONS

This application is a § 371 national stage entry of International Application No. PCT/FR2020/050031, filed Jan. 10, 2020, which claims priority to French Patent Application No. FR1900252, filed Jan. 10, 2019, the entire contents of which are incorporated herein by reference.

TECHNICAL FIELD OF THE INVENTION

The invention relates to a thickening composition comprising at least one oil derived from a biological source and one poly(farnesene) polymer.

The invention also relates to a cosmetic composition comprising said thickening composition and use thereof.

The present invention also relates to the use of said thickening composition for the formulation of cosmetic products.

STATE OF THE ART

Cosmetic products exist in various different forms. They may be either in the form of emulsions (a mixture of an aqueous phase with a fatty phase stabilised by an emulsifier), or entirely aqueous, or entirely anhydrous (only a fatty phase). In order to texturise or increase the viscosity of the fatty phase, either in an emulsion or in an anhydrous product, the person skilled in the art would use a thickener for the fatty phase which may be a gel, that is to say a mixture of an non-polar (or apolar) oil and a gelling agent. These gels are particularly used for the formulation of lip gloss, lip moisturiser, skin cream or sunscreen products. But they are also found in hair products, depilatory creams and deodorants.

Thus, a non-polar or apolar gel is a mixture of a non-polar oil and a gelling agent. The non-polar oils may be mineral oils, plant oils, silicone oils, or isoparaffins. The gelling agent is most often polymeric such as ethylene/propylene styrene copolymer, or butylene/ethylene/styrene copolymer, or polyisobutene, polydecene, or isoprene copolymers (or even SEBS, SBS, SIS, TPE, etc). These copolymers are typically sold by the companies Kraton or Kuraray.

The most commonly used gels are mineral oil based gels. There is a very high degree of compatibility between these oils and the copolymers; in fact the non-polar structure of the copolymers is highly compatible with these oils. The gels that are mineral oil based present the following major drawbacks: the oil is derived from fossil-based sources and the product has a somewhat runny texture.

Document WO 2018/172228 describes a gelled composition comprising a hydrocarbon oil from a biological source and a gelling polymer from fossil-based source. The hydrocarbon oil and the gelling polymer are mixed at temperatures that are higher than 40° C., in order to enable the obtaining of the gelled composition.

The documents U.S. Pat. No. 9,334,394 and US 2015/0051332 describe rubber compositions comprising a polymer of the type poly(farnesene). These compositions are not suitable for topical application on the skin, nails or skin appendages.

The document US 2013/0251846 describes chewing gum compositions intended for oral administration. This document does not disclose compositions that are suitable intended for topical application on the skin, nails or skin appendages. This document discloses compositions comprising a poly(farnesene) polymer that has a weight average molecular mass greater than 450,000 g/mol.

There therefore remains a need to provide a thickening composition that may be obtained by mixing at ambient temperature, typically a temperature that is lower than 40° C., more particularly lower than 30° C., and which exhibits good gloss and sensory properties.

The Applicant has in a surprising manner found that this need can be satisfied by a novel thickening composition having a fatty phase derived from a biological source and a bio-based (biosourced) polymer of a type such as poly (farnesene).

The object of the present invention is also to provide a thickening composition that is made from raw materials derived from biological sources, in particular where the fatty phase is derived from a biological source.

The object of the present invention is also to provide a stable thickening composition having properties that are appropriate to the use thereof.

SUMMARY OF THE INVENTION

These objectives are achieved thanks to a novel thickening composition.

The invention relates to a thickening composition comprising:
At least one oil derived from a biological source, and
At least one poly(farnesene) polymer having a number average molar mass ranging from 10,000 to 120,000 g/mol.

According to one embodiment, the oil derived from a biological source is selected from among hydrocarbon oils, plant or animal oils in the form of acids, esters or amides, and mixtures thereof.

According to one embodiment, the oil derived from a biological source is a hydrocarbon oil, preferably comprising a content by weight of isoparaffins ranging from 90 to 100%, a content by weight of normal paraffins ranging from 0 to 10%, and a content of carbon derived from biological sources preferably greater than or equal to 90% relative to the total weight of the hydrocarbon oil.

Preferably, the hydrocarbon oil is selected from among non-cyclic isoparaffins comprising from 14 to 18 carbon atoms.

Preferably, the hydrocarbon oil comprises:
a content by weight of isoparaffins, ranging from 95 to 100% and preferentially from 98% to 100% relative to the total weight of the hydrocarbon oil; and/or
a content of carbon derived from biological sources that is greater than or equal to 95%, preferably greater than or equal to 98%, and preferentially 100%; and/or
a content by weight of normal paraffins that is less than or equal to 10, preferably less than or equal to 5%, and preferentially less than or equal to 2% relative to the total weight of the hydrocarbon oil; and/or
a content by weight of naphthenic compounds that is less than or equal to 1%, preferably less than or equal to 0.5%, and preferentially less than or equal to 100 ppm relative to the total weight of the hydrocarbon oil; and/or
a content by weight of aromatic compounds that is less than or equal to 500 ppm, preferably less than or equal to 300 ppm, preferentially less than or equal to 100 ppm, more preferentially less than or equal to 50 ppm, and advantageously less than or equal to 20 ppm, relative to the total weight of the hydrocarbon oil.

Preferably, the hydrocarbon oil is obtained by a method of catalytic hydrogenation at a temperature of 80 to 180° C., and at a pressure of 50 to 160 bars of a deoxygenated and/or isomerised biologically-sourced feedstock.

According to one embodiment, the poly(farnesene) polymer has a number average molar mass ranging from 20,000 to 110,000 g/mol, preferably from 30,000 to 100,000 g/mol, more preferably from 40,000 to 90,000 g/mol, more preferentially from 50,000 to 80,000 g/mol.

According to one embodiment, the poly(farnesene) polymer has a number average molar mass ranging from 10,000 to 95,000 g/mol, preferably from 15,000 to 90,000 g/mol, more preferably from 20,000 to 85,000 g/mol, more preferentially from 30,000 to 80,000 g/mol.

According to one embodiment, the poly(farnesene) polymer is partially or fully hydrogenated and/or the poly(farnesene) polymer is functionalised with hydroxyl groups.

According to one embodiment, the thickening composition comprises, relative to the total weight of the thickening composition:
  from 10 to 90% by weight, preferably from 20 to 80% by weight, more preferably from 30 to 70% by weight, even more preferentially from 40 to 60% by weight, of oil(s) derived from biological sources; and
  from 10 to 90% by weight, preferably from 20 to 80% by weight, more preferably from 30 to 70% by weight, even more preferentially from 40 to 60% by weight, of poly(farnesene) polymer(s).

The present invention also relates to the use of the thickening composition according to the invention, as a thickening agent, sensory agent, film-forming agent, texturing agent, water resistance enhancing agent, moisturising/hydrating agent, conditioner, viscous oil, or agent that provides a second skin effect, in a cosmetic composition that preferably comprises at least one fatty substance.

The object of the present invention also relates to a cosmetic composition comprising at least one thickening composition according to the invention, preferably in an amount ranging from 1 to 80%, preferentially from 5 to 70%, and advantageously from 10 to 50% by weight, relative to the total weight of the cosmetic composition.

According to one embodiment, the cosmetic composition according to the invention comprises at least one fatty substance selected from among: plant oils, where appropriate other than the plant oils of said thickening composition; hydrocarbon oils, where appropriate other than the hydrocarbon oil of said thickening composition; plant butters: fatty ethers and fatty alcohols; oily esters; alkanes and silicone oils; and/or at least one additive preferably selected from emulsifiers.

Another object of the present invention relates to the use of the thickening composition according to the invention, or use of the cosmetic composition according to the invention, for topical application, in particular as a care product for the skin or the hair, as a makeup product, as a hair product, as a makeup removal product, as a perfumed product, as a sunscreen product, as a lip care product, such as a lip gloss or moisturising sticks for the lips.

Finally, the object of the invention relates to a cosmetic treatment process for the cosmetic treatment of the skin, lips or skin appendages, which comprises at least one step of applying, preferably by spreading, the thickening composition according to the invention or the cosmetic composition according to the invention, on the skin, the lips or skin appendages.

The thickening composition according to the invention makes it possible to obtain a composition that is classified as non-irritant, biodegradable and odourless.

The thickening composition according to the invention is derived from bio-based sources.

The thickening composition according to the invention may be obtained by the simple mixing at ambient temperature, of an oil derived from a biological source and a polymer derived from a biological source.

The thickening composition according to the invention may be used as a sensory agent in cosmetic compositions, in particular in the fatty phases of cosmetic compositions.

The thickening composition according to the invention may be used as a gloss agent in cosmetic compositions, such as lip glosses.

The thickening composition according to the invention may be used as a film-forming agent, viscous oil, thickener, texturing agent.

DETAILED DESCRIPTION OF THE INVENTION

The invention relates to a thickening composition intended for topical application on the skin, nails or skin appendages (including the lips, the hair and scalp), said thickening composition comprising:
  From 10 to 90% by weight of at least one oil derived from a biological source; and
  From 10 to 90% by weight of at least one poly(farnesene) polymer having a number average molar mass ranging from 10,000 to 120,000 g/mol, preferably from 10,000 to 95000 g/mol, relative to the total weight of the thickening composition.

As a preliminary matter, it should be noted that, in the description and the claims following below, the term "(comprised) between" is to be understood as including the limits or bounds mentioned.

Oil Derived from Biological Sources

The oil derived from a biological source used in the thickening composition according to the invention may be selected from among:
  hydrocarbon oils derived from biological sources;
  plant or animal oils selected from among C6 to C24 fatty acids in acid, ester or amide form, preferably in acid or ester form;
  and a mixture thereof.

Plant or Animal Oils

According to one embodiment, the oil derived from a biological source is selected from among plant or animal oils selected from among C6 to C24 fatty acids in acid, ester or amide form, preferably from C6 to C24 fatty acids in acid or ester form.

The term "fatty acid ester or amide" is understood to refer to the products defined as follows:
  A fatty acid ester is the product of reaction between at least one fatty acid and at least one alcohol derived from a biological source, this alcohol possibly being a monoalcohol, whether linear or branched, comprising from 1 to 6 carbon atoms; or a polyol, whether linear or branched, comprising from 2 to 5 hydroxyl groups; preferably a trimethylolpropane, an erythritol, a pentaerythritol, a glycol, and/or a glycerol. It is thus possible to obtain monoesters, diesters, triesters, tetraesters or pentaesters. Included in this definition are plant oils themselves and the transesterification products thereof.

A fatty acid amide is the product of reaction between at least one fatty acid and at least one primary, secondary or tertiary amine or polyamines derived from biological source comprising from 2 to 6 amino groups.

Among the compounds of plant origin, the following will be selected: the acids, esters or amides of tall oil, rapeseed oil, sunflower oil, castor oil, peanut oil, flax oil, copra oil, olive oil, palm oil, cotton oil, corn oil, tallow oil, lard oil, palm kernel oil, soybean oil, squash seed oil, grape seed oil, argan oil, jojoba oil, sesame oil, walnut oil, hazelnut oil, Chinese wood oil, rice oil, as well as oils of the same type derived from hybrid or genetically modified species.

Among the compounds of animal origin, mention may be made of acids, esters and amides of fats from marine animals, fish or marine mammals and fats from land animals such as equine, bovine, and porcine fats.

The preferred fatty acids are of tall oil (tall oil fatty acids or TOFA, as per common terminology), containing from 0.5 to 10% by weight of resin acid and ester derivatives thereof that are methanol, ethanol, glycol, and glycerol based.

Also preferred are triglycerides and other esters of soybean oil and rapeseed oil, including oils of hybrids or genetically modified species thereof.

The oil of plant or animal origin used according to the invention may also be selected from among vegetable oil methyl esters (VOME).

Thus, according to one particular embodiment, the oil of plant or animal origin that is used according to the invention is selected from among vegetable oil methyl esters (VOME), fatty acids of tall oil (tall oil fatty acids or TOFA, as per common terminology), and the mixtures thereof.

The oil derived from a biological source that is used in the invention typically has a biomaterial content of at least 90%. This content is advantageously higher, in particular greater than or equal to 95%, preferably greater than or equal to 98%, and advantageously equal to 100%. The determination of the biomaterial or bio-carbon content is given in accordance with the standards ASTM D 6866-12, method B (ASTM D 6866-06) and ASTM D 7026 (ASTM D 7026-04).

The term "bio-carbon" is understood to indicate that the carbon is of natural origin and comes from a biomaterial, as indicated below. The terms "bio-carbon content" and "biomaterial content" are expressions that indicate the same value. A material derived from a renewable source or biomaterial, is an organic material in which the carbon is obtained from $CO_2$ fixed recently (on a human scale) by photosynthesis from the atmosphere. A biomaterial (100% carbon of natural origin) has a $^{14}C/^{12}C$ isotopic ratio that is greater than $10^{-12}$, typically around $1.2 \times 10^{-12}$, whereas a fossil material has a zero ratio. In fact, the $^{14}C$ isotope is formed in the atmosphere and is then integrated by photosynthesis, based on a time scale of a few decades at most. The half-life of $^{14}C$ is 5730 years. Thus, the materials resulting from photosynthesis, namely plants in general, necessarily have a maximum $^{14}C$ isotope content.

Hydrocarbon Oils

According to one preferred embodiment, the oil derived from a biological source used in the thickening composition according to the invention is a hydrocarbon oil.

Preferably, the hydrocarbon oil comprises molecules having from 8 to 30 carbon atoms, preferably from 12 to 30 carbon atoms, more preferably from 13 to 19 carbon atoms, or indeed even from 14 to 18 carbon atoms.

The thickening composition according to the invention preferably comprises a hydrocarbon oil content ranging from 10 to 90% by weight, preferentially from 20 to 80% by weight, more preferably from 30 to 70% by weight, and advantageously from 40 to 60% by weight relative to the total weight of the composition.

The presence of a significant amount of hydrocarbon oil according to the invention contributes to the cosmetic qualities of the thickening composition: pleasant to the feel, care, gloss, and protection to the skin.

The hydrocarbon oil of the thickening composition according to the invention preferably comprises a content by weight of isoparaffinic compounds that is greater than or equal to 90%, preferably greater than or equal to 95%, and advantageously greater than or equal to 98% relative to the total weight of hydrocarbon oil.

According to one embodiment, the isoparaffinic compounds present in the hydrocarbon oil used according to the invention contain from 12 to 30 carbon atoms, preferably from 13 to 19 carbon atoms, more preferably from 14 to 18 carbon atoms.

The hydrocarbon oil of the thickening composition according to the invention preferably comprises a content by weight of normal paraffins that is less than or equal to 10%, preferentially less than or equal to 5%, and advantageously less than or equal to 2%.

The hydrocarbon oil of the thickening composition according to the invention advantageously comprises a majority of isoparaffins and a minority of normal paraffins.

These isoparaffins are advantageously non-cyclic isoparaffins. Preferably the hydrocarbon oil of the thickening composition has a mass ratio of isoparaffins to normal paraffins of at least 12:1, preferentially 15:1 and more preferentially 20:1. Even more advantageously, the hydrocarbon oil of the thickening composition according to the invention does not contain normal paraffins.

According to one embodiment, the hydrocarbon oil according to the invention preferably comprises a content by weight of isoparaffins ranging from 90 to 100% and a content of normal paraffins ranging from 0 to 10%, preferentially from 95 to 100% of isoparaffins and from 0 to 5% of normal paraffins, and more preferentially from 98% to 100% of isoparaffins and from 0 to 2% of normal paraffins.

According to one embodiment, the hydrocarbon oil of the thickening composition according to the invention preferably comprises a content by weight of isoparaffins ranging from 90 to 100% and a content of normal paraffins ranging from 0 to 10%, preferentially from 95 to 100% of isoparaffins selected from among alkanes comprising from 12 to 30 carbon atoms, preferably from 13 to 19 carbon atoms, more preferably from 14 to 18 carbon atoms.

According to one embodiment, the hydrocarbon oil that is used according to the invention comprises:
  isoparaffins having 15 carbon atoms, and isoparaffins having 16 carbon atoms in a combined amount ranging from 80 to 98% by weight, relative to the total weight of the hydrocarbon oil, or
  isoparaffins having 16 carbon atoms, isoparaffins having 17 carbon atoms, and isoparaffins having 18 carbon atoms in a combined amount ranging from 80 to 98% by weight, relative to the total weight of the hydrocarbon oil, or
  isoparaffins having 17 carbon atoms, and isoparaffins having 18 carbon atoms in a combined amount ranging from 80 to 98% by weight, relative to the total weight of the hydrocarbon oil.

The hydrocarbon oil of the thickening composition according to the invention preferably comprises a content by weight of naphthenic compounds that is less than or equal to 1%, preferentially less than or equal to 0.5% and more preferentially less than or equal to 100 ppm.

According to another preferred embodiment, the hydrocarbon oil of the thickening composition according to the invention comprises a content by weight of isoparaffins ranging from 90 to 100%, a content by weight of normal paraffins ranging from 0 to 10%, and a content by weight of naphthenes that is less than or equal to 1%. Preferentially, the hydrocarbon oil comprises a content by weight ranging from 95 to 100% of isoparaffins, from 0 to 5% of normal paraffins and a content by weight of naphthenes that is less than or equal to 0.5%. More preferentially, it comprises a content by weight ranging from 98% to 100% of isoparaffins, from 0 to 2% of normal paraffins, and a content by weight of naphthenes that is less than or equal to 100 ppm.

The hydrocarbon oil used in the thickening composition according to the invention is advantageously free of aromatic compounds. For example, it is intended for the content by weight of aromatic compounds to be less than or equal to 500 ppm, preferably less than or equal to 300 ppm, preferentially less than or equal to 100 ppm, more preferentially less than or equal to 50 ppm, and advantageously less than or equal to 20 ppm measured for example by UV spectrometry.

The content by weight of isoparaffins, n-paraffins, naphthenes and/or aromatics in the hydrocarbon oil may be determined according to methods that are well known to the person skilled in the art. By way of non-limiting example, mention may be made of a method involving gas chromatography.

According to another preferred embodiment, the hydrocarbon oil of the thickening composition according to the invention comprises a content by weight of isoparaffins ranging from 90 to 100%, a content by weight of normal paraffins ranging from 0 to 10%, a content by weight of naphthenes that is less than or equal to 1%, and a content by weight of aromatic compounds that is less than or equal to 500 ppm. Preferentially the hydrocarbon oil comprises a content by weight ranging from 95 to 100% of isoparaffins, from 0 to 5% of normal paraffins, a content by weight of naphthenes that is less than or equal to 0.5%, and a content by weight of aromatic compounds that is less than or equal to 300 ppm, preferably less than 100 ppm, preferentially less than 50 ppm, and advantageously less than 20 ppm. Preferentially also the hydrocarbon oil comprises a content by weight ranging from 95 to 100% of isoparaffins, from 0 to 5% of normal paraffins, and a content by weight of aromatic compounds that is less than or equal to 100 ppm. More preferentially, it comprises a content by weight ranging from 98% to 100% of isoparaffins, from 0 to 2% of normal paraffins, a content by weight of naphthenes that is less than or equal to 100 ppm and a content by weight of aromatic compounds that is less than or equal to 100 ppm.

The hydrocarbon oil that is implemented in the thickening composition according to the invention also preferably has an extremely low content by weight of sulfur compounds, typically less than or equal to 5 ppm, preferentially less than or equal to 3 ppm, and more preferentially less than or equal to 0.5 ppm, that is to say at a level too low to be detected by means of conventional low-sulfur analysers.

The hydrocarbon oil that is implemented in the thickening composition according to the invention also preferably has a flash point that is greater than or equal to 110° C., preferentially greater than or equal to 120° C., and more preferentially greater than or equal to 140° C. according to the standard EN ISO 2719. A high flash point, typically greater than 110° C. makes it possible, among other things, to alleviate on the one hand the safety problems during storage and transport by avoiding excessively sensitive flammability of the hydrocarbon oil.

The hydrocarbon oil also preferably has a vapour pressure at 20° C. that is less than or equal to 0.01 kPa.

According to one embodiment, the hydrocarbon oil that is implemented in the thickening composition according to the invention also preferably has a flash point that is greater than or equal to 110° C. according to the standard EN ISO 2719, and a vapour pressure at 20° C. that is less than or equal to 0.01 kPa. Preferentially, the hydrocarbon oil has a flash point that is greater than or equal to 120° C., and a vapour pressure at 20° C. that is less than or equal to 0.01 kPa. And more preferentially, it has a flash point that is greater than or equal to 130° C., and a vapour pressure at 20° C. that is less than or equal to 0.01 kPa.

The hydrocarbon oil that is implemented in the thickening composition according to the invention exhibits boiling point temperatures, a flash point and a vapour pressure that make it possible to overcome the problems of flammability, odour, and volatility.

The hydrocarbon oil of the thickening composition according to the invention in addition preferably has a kinematic viscosity at 40° C. that is less than or equal to 5 cSt, preferentially less than or equal to 4 cSt, and more preferentially less than or equal to 3 cSt according to the standard. EN ISO 3104.

According to one particular embodiment, the hydrocarbon oil has:
- a boiling point ranging from 230 to 340° C., preferably from 235 to 330° C., and more preferentially from 240 to 325° C. according to the standard ASTM D86; and/or
- a biodegradability at 28 days of at least 60%, preferably at least 70%, preferentially at least 75%, and even more preferentially at least 80% measured according to the standard OECD 306; and/or
- a flash point that is greater than or equal to 110° C. according to standard EN ISO 2719.

Method for Obtaining Hydrocarbon Oil:

Such compositions of hydrocarbon oils may be obtained in the follow manner. The hydrocarbon oil according to the invention is a hydrocarbon fraction which is derived from the conversion of biomass.

The term "derived from the conversion of biomass" is understood to refer to a hydrocarbon fraction produced from raw materials derived from biological sources.

Preferably, the hydrocarbon fraction derived from a biological source is obtained by a method that comprises the steps of hydrodeoxygenation (HDO) and isomerisation (ISO). The hydrodeoxygenation (HDO) step results in the decomposition of the structures of the biological esters or of the triglyceride constituents, the elimination of oxygenated, phosphorus and sulfur compounds, and the hydrogenation of the olefinic bonds. The product resulting from the hydrodeoxygenation reaction is subsequently isomerised. A fractionation step may preferably follow the hydrodeoxygenation and isomerisation steps. In an advantageous manner, the fractions of interest are thereafter subjected to the steps of hydrotreatment then followed by distillation in order to obtain the specifications of the desired hydrocarbon oil according to the invention.

This HDO/ISO method is implemented on a crude biological feedstock, also know as biomass or raw material of biological origin, that is selected from the group consisting of plant oils, animal fats, fish oils and the mixtures thereof. Appropriate raw materials of biological origin are, for example, rapeseed oil, canola oil, tall oil, sunflower oil, soybean oil, hemp oil, olive oil, linseed oil, mustard oil, palm oil, peanut oil, castor oil, coconut oil, animal fats such as tallow, recycled dietary fats, raw materials derived from genetic engineering, and biological raw materials produced from microorganisms such as algae and bacteria. Condensation products, esters or other derivatives obtained from crude biological materials may also serve as raw materials.

Preferably, the raw material of biological origin is an ester or a triglyceride derivative. This material is first of all subjected to a hydrodeoxygenation (HDO) step in order to decompose the structure of the constituent esters or triglycerides and to eliminate the oxygenated, phosphorus and sulfur compounds concomitantly with the hydrogenation of the olefinic bonds. This step of hydrodeoxygenation (HDO) of the raw material of biological origin is followed by an isomerisation of the product thus obtained leading to the branching of the hydrocarbon chain and to an improvement in the properties of the paraffin at low temperatures.

During the HDO step, the hydrogen and the raw material of biological origin are passed over a hydrodeoxygenation catalyst bed in a simultaneous fashion, in a co-current or counter-current manner. During the HDO step, the pressure and the temperature are between 20 and 150 bars and between 200 and 500° C. respectively. Conventional and known hydrodeoxygenation catalysts are used during this step. Optionally, the raw material of biological origin may be subjected to a pre-hydrogenation under mild conditions in order to prevent the secondary reactions of double bonds before the HDO step. After the hydrodeoxygenation step, the product resulting from the reaction is subjected to a step of isomerisation (ISO) where the hydrogen and the product, and optionally a mixture of n-paraffins, are passed through isomerisation catalyst beds in a simultaneous fashion, in a co-current or counter-current manner. During the ISO step, the pressure and the temperature are between 20 and 150 bars and between 200 and 500° C. respectively. Conventional and known isomerisation catalysts are used during this step.

Additional secondary methods may also be implemented (such as intermediate mixtures, traps or other similar sorts of methods).

The product resulting from the HDO/ISO steps can optionally be fractionated in order to obtain the fractions of interest.

Various HDO/ISO methods are described in the literature. The application WO2014/033762 describes a method comprising a pre-hydrogenation step, a hydrodeoxygenation (HDO) step and an isomerisation step that runs counter-current. The patent application EP1728844 describes a hydrocarbon production method for producing hydrocarbon compounds from a mixture of compounds of plant and animal origin. This method comprises a pretreatment step for pretreating the mixture that makes it possible to remove the contaminants, such as for example the alkali metal salts, followed by a hydrodeoxygenation (HDO) step and an isomerisation step. The patent application EP2084245 describes a hydrocarbon production method for producing a hydrocarbon mixture which may be used as gas oil or in a gas oil composition by hydrodeoxygenation of a mixture derived from biological sources containing esters of fatty acids optionally mixed with free fatty acids, for example plant oils such as sunflower oil, rapeseed oil, canola oil, palm oil, or tall oil, followed by hydroisomerisation on specific catalysts. The patent application EP2368967 describes such a method and the product obtained by this method. The application WO2016/185046 describes a method for obtaining a hydrocarbon oil used according to the invention, in which the hydrocarbon oil is obtained by a method of catalytic hydrogenation at a temperature of 80 to 180° C. and at a pressure of 50 to 160 bars of a feedstock derived from deoxygenated and isomerised biological source.

Advantageously, the raw material of biological origin contains less than 15 ppm of sulfur, preferably less than 8 ppm, preferably less than 5 ppm, and more preferentially less than 1 ppm according to the standard EN ISO 20846. Ideally, the feedstock does not include sulfur as a raw material derived from bio-based sources.

Prior to the hydrotreatment step, a pre-fractionation step may take place. A narrower fraction at the inlet of the hydrogenation unit makes it possible to obtain a narrow fraction at the outlet of the unit. Indeed, the boiling points of pre-fractionated fractions are comprised between 220 and 330° C. while the fractions which have not been pre-fractionated typically have boiling points comprised between 150 and 360° C.

The deoxygenated and isomerised feedstock from the HDO/ISO method is then hydrogenated.

The hydrogen used in the hydrogenation unit is typically highly purified hydrogen. The term "highly purified" is understood to refer to hydrogen having a purity for example that is greater than 99%, even though other grades may also be used.

The hydrogenation step is carried out by making use of catalysts. The typical hydrogenation catalysts may be either bulk catalysts or supported catalysts and may include the following metals: nickel, platinum, palladium, rhenium, rhodium, nickel tungstate, nickel-molybdenum, molybdenum, cobalt-molybdenum. The supports may be silica, alumina, silica-alumina or zeolites.

A preferred catalyst is an alumina-supported nickel based catalyst, of which the specific surface area varies between 100 and 200 m$^2$/g of catalyst or a nickel based bulk catalyst. The hydrogenation conditions are typically as follows:

Pressure: 50 to 160 bars, preferably 80 to 150 bars, and more preferentially 90 to 120 bars;

Temperature: 80 to 180° C., preferably 120 to 160° C., and more preferentially 150 to 160° C.;

Liquid Hourly Space velocity (LHSV): 0.2 to 5 hr$^{-1}$, preferably 0.4 to 3 hr$^{-1}$ and more preferentially 0.5 to 0.8 hr$^{-1}$;

Hydrotreatment (hydrogen treatment) rate: adapted to the conditions mentioned hereinabove and able to range up to 200 Nm$^3$/tonnes of feedstock to be treated.

The temperature in the reactors is typically between 150 and 160° C. with a pressure of about 100 bars while the liquid hourly space velocity is about 0.6 hr$^{-1}$ with a treatment rate that is appropriately adjusted according to the quality of the feedstock to be treated and the parameters of the first hydrogenation reactor.

The hydrogenation may take place in one or more reactors in series. The reactors may include one or more catalytic beds. The catalytic beds are generally stationary catalytic beds.

The hydrogenation method preferably comprises two or three reactors, preferably three reactors and is more preferentially carried out in three reactors in series.

The first reactor allows for the trapping of the sulfur compounds and the hydrogenation of essentially all of the unsaturated compounds and up to about 90% of the aromatic compounds. The product coming from the first reactor contains substantially no sulfur compound. In the second stage, that is to say in the second reactor, the hydrogenation of the aromatics continues and due to this up to 99% of the aromatics are thus hydrogenated.

The third stage in the third reactor is a finishing stage that provides the means to obtain aromatics content levels of less than or equal to 500 ppm, preferably less than or equal to 300 ppm, preferentially less than or equal to 100 ppm, more preferentially less than or equal to 50 ppm, and ideally less than or equal to 20 ppm even in the case of products with a high boiling point, for example greater than 300° C.

It is possible to use a reactor which includes two or three or more catalytic beds. The catalysts may be present in amounts that are variable or substantially equal in each reactor; for three reactors, the quantities depending on the weight for example may be 0.05-0.5/0.10-0.70/0.25-0.85, preferably 0.07-0.25/0.15-0.35/0.4-0.78, and more preferentially 0.10-0.20/0.20-0.32/0.48-0.70.

It is also possible to use one or two hydrogenation reactors instead of three.

It is also possible for the first reactor to be comprised of twin reactors that are operated in an alternating manner. This mode of operability in particular allows for the facilitated loading and unloading of the catalysts: when the first reactor comprises the catalyst that is saturated first (substantially all the sulfur is trapped on and/or in the catalyst) it has to be changed often.

A single reactor may also be used in which two, three or more catalytic beds are installed.

It may be necessary to insert quench boxes (pertaining to "quenching of the reaction") in the recycling system or between the reactors in order to cool the effluents from one reactor to another or from one catalytic bed to another in order to control the temperatures and the hydrothermal equilibrium of each reaction. According to one preferred embodiment, there are no cooling or quenching intermediates.

According to one embodiment, the product resulting from the method and/or the separated gases are at least partially recycled in the feed system of the hydrogenation reactors. This dilution contributes to maintaining the exothermicity of the reaction within controlled limits, in particular at the first stage. The recycling furthermore serves to enable a heat exchange before the reaction and as well as better control of the temperature.

The effluent from the hydrogenation unit mainly contains the hydrogenated product and hydrogen. Flash separators are used to separate the effluents into the gaseous phase, mainly residual hydrogen, and into the liquid phase, mainly the hydrogenated hydrocarbon fractions. The method can be carried out by using three flash separators, one at high pressure, one at intermediate pressure, and one at low pressure very close to the atmospheric pressure.

The gaseous hydrogen which is collected at the top of the flash separators may be recycled in the feed system of the hydrogenation unit or at various different levels in the hydrogenation units between the reactors.

According to one embodiment, the final product is separated at atmospheric pressure. It then directly feeds a vacuum fractionation unit. Preferably, the fractionation will be carried out at a pressure of between 10 and 50 mbars and more preferentially at about 30 mbars.

The fractionation may be carried out in a manner such that it is possible to simultaneously withdraw various hydrocarbon fluids from the fractionation column and such that their boiling point can be predetermined.

By adapting the feedstock through its initial and final boiling points, the hydrogenation reactors, the separators and the fractionation unit can therefore be directly connected without it being necessary to use intermediate tanks. This integration of the hydrogenation and the fractionation allows for an optimised thermal integration combined with both with a reduction in the number of devices and with energy savings.

The hydrocarbon oil that is implemented in the thickening composition of the invention is advantageously a hydrocarbon fraction having a distillation range DR (in ° C.) ranging from 230° C. to 340° C., preferably from 235° C. to 330° C., and more preferentially from 240° C. to 325° C. measured according to the standard ASTM D86. Preferably, the difference between the initial boiling point and the final boiling point is less than or equal to 80° C., preferably less than or equal to 70° C., more preferentially less than or equal to 60° C., and advantageously between 40 and 50° C. The hydrocarbon oil may comprise one or more fractions of distillation ranges comprised within the ranges described here above.

Advantageously, the hydrocarbon oil that is implemented in the thickening composition of the invention is completely saturated. Preferably, the components of the hydrocarbon oil are selected from among isoparaffins that comprise 12 to 30 carbon atoms, preferably 13 to 19 carbon atoms, and more preferentially 14 to 18 carbon atoms.

The thickening composition according to the invention advantageously comprises an isohexadecane content by weight of less than or equal to 50%.

The hydrocarbon oil of the thickening composition according to the invention is ideally obtained as a result of the processing of raw materials derived from biological sources.

The hydrocarbon oil of the thickening composition according to the invention typically has a biomaterial content of at least 90%. This content is advantageously higher, in particular greater than or equal to 95%, preferably greater than or equal to 98%, and advantageously equal to 100%.

In addition to a particularly high biomaterial content, the hydrocarbon oil of the thickening composition according to the invention has particularly good biodegradability. The biodegradation of an organic chemical product refers to the reduction in the complexity of chemical compounds thanks to the metabolic activity of microorganisms. Under aerobic conditions, the microorganisms convert the organic substances transforming them into carbon dioxide, water and biomass. The OECD 306 test method, is used for the evaluation of the biodegradability of individual substances in seawater. According to this method, the hydrocarbon oil has a biodegradability at 28 days of at least 60%, preferably of at least 70%, more preferably of at least 75%, and more preferentially of at least 80%.

Poly(Farnesene) Polymer:

The poly(farnesene) that is implemented in the present invention is typically a farnesene polymer which may be partially or fully hydrogenated and/or which may be functionalised, in particular at the end of the chain, for example by hydroxyl groups.

Farnesene exists in the form of different isomers, such as alpha-farnesene and beta-farnesene. Beta-farnesene may be represented by the following formula (I):

[Chem 1]

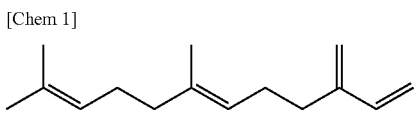

According to the invention, the poly(farnesene) has a number average molar mass ranging from 10,000 to 120,000 g/mol, preferably from 20,000 to 110,000 g/mol, more preferably from 30,000 to 100,000 g/mol, preferentially from 40,000 to 90,000 g/mol, more preferentially from 50,000 to 80,000 g/mol. According to one embodiment, the poly(farnesene) has a number average molar mass ranging from 10,000 to 90,000 g/mol, preferably from 20,000 to 80,000 g/mol. The number average molar mass can be measured by means of chromatography over permeable gel ("gel permeation chromatography" as per accepted terminology), by using polystyrene standards. The poly(farnesene) used in the invention may exhibit a viscosity at 25° C. ranging from 20,000 to 1,000,000 mPa·s, preferably from 50,000 to 800,000 mPa·s, more preferably from 100,000 to 600,000 mPa·s.

Typically, the polymer used in the invention is a homopolymer of beta-farnesene.

The poly(farnesene) used according to the invention may comprise n monomers having the formula (II) and/or m monomers having the formula (III):

[Chem 2]

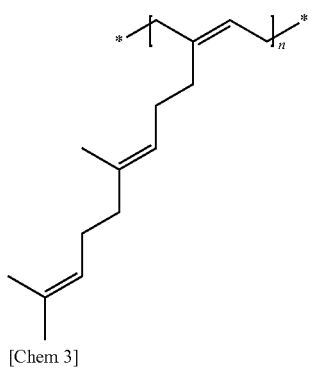

(II)

[Chem 3]

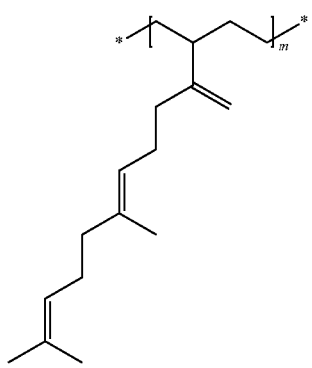

(III)

Wherein n and m are independently of each other, whole numbers ranging for example from 40 to 600.

According to one particular embodiment, the poly(farnesene) used according to the invention consists of monomers having the formula (II) and/or of monomers having the formula (III) as defined here above.

The poly(farnesene) used according to the invention may be functionalised at the chain-end, for example with one or two hydroxyl functions.

According to one particular embodiment, the poly(farnesene) used according to the invention is partially or fully hydrogenated. The term "partially hydrogenated poly(farnesene)" is used to refer to a poly(farnesene) that comprises at least one unsaturation but whereof a portion of the unsaturations has been hydrogenated. The term "fully hydrogenated poly(farnesene)" is used to refer to a saturated poly(farnesene) which no longer comprises unsaturations.

According to one embodiment, the polymer used in the invention is a fully hydrogenated poly(farnesene).

Thus, according to one embodiment of the invention, the poly(farnesene) polymer used according to the invention comprises n monomers having the formula (II bis) and m monomers having the formula (III bis):

[Chem 4]

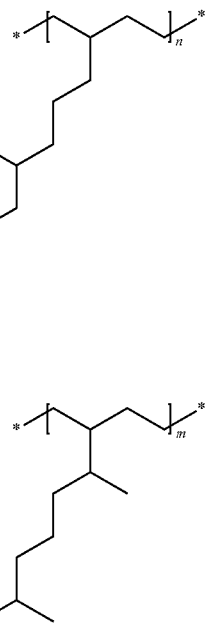

(II bis)

[Chem 5]

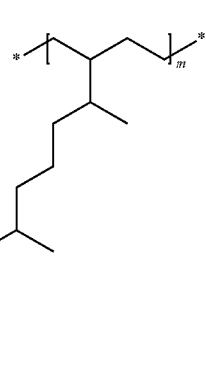

(III bis)

wherein n and m have the same significance as mentioned here above.

According to one particular embodiment, the poly(farnesene) used according to the invention consists of: monomers having the formula (II), and/or monomers having the formula (III), and/or monomers having the formula (II bis), and/or monomers having the formula (III bis), as defined here above.

The inventors have discovered that the poly(farnesene) having a number average molar mass ranging from 10,000 to 120,000 g/mol, in particular from 10,000 to 90,000 g/mol, effectively served to enhance the gloss of an oil, in particular of an oil derived from a biological source. Enhancement of the gloss may be assessed by increasing the refractive index.

Manufacturing Method for Manufacturing the Poly(Farnesene) Polymer:

The poly(farnesene) is obtained from farnesene derived from biological sources. Farnesene may be obtained from insects or plants or by culturing microorganisms. Farnesene derived from biological sources is commercially available, for example from the company Amyris.

The poly(farnesene) may be obtained by any known method of polymerisation, for example by anionic polymerisation which serves to enable more precise control of the molecular mass of the polymer obtained. The polymerisation may be carried out in batch or continuous process with the progressive addition of the possible initiator, the monomers, and the possible solvent.

The temperature during the polymerisation process may range from −80 to 80° C.

The poly(farnesene) may be obtained by a method described in the patent document WO2018/052709, from page 5, line 3 to page 6, line 17.

Thickening Composition:

According to one embodiment of the invention, the thickening composition according to the present invention comprises:
- from 10 to 90% by weight, preferably from 20 to 80% by weight, preferentially from 30 to 70% by weight, more preferentially from 40 to 60% by weight, of oil(s) derived from biological sources, and
- from 10 to 90% by weight, preferably from 20 to 80% by weight, preferentially from 30 to 70% by weight, more preferentially from 40 to 60% by weight, of poly(farnesene) polymer(s) having a number average molar mass ranging from 10,000 to 120,000 g/mol, relative to the total weight of the thickening composition.

According to one embodiment of the invention, the thickening composition according to the present invention comprises:
- from 10 to 90% by weight, preferably from 20 to 80% by weight, preferentially from 30 to 70% by weight, more preferentially from 40 to 60% by weight, of hydrocarbon oil(s) as defined here above; and
- from 10 to 90% by weight, preferably from 20 to 80% by weight, preferentially from 30 to 70% by weight, more preferentially from 40 to 60% by weight, of poly(farnesene) polymer(s) having a number average molar mass ranging from 10,000 to 120,000 g/mol, relative to the total weight of the thickening composition.

According to one embodiment of the invention, the thickening composition according to the present invention comprises:
- from 10 to 90% by weight, preferably from 20 to 80% by weight, preferentially from 30 to 70% by weight, more preferentially from 40 to 60% by weight, of oil(s) derived from biological sources; and
- from 10 to 90% by weight, preferably from 20 to 80% by weight, preferentially from 30 to 70% by weight, more preferentially from 40 to 60% by weight, of poly(farnesene) polymer(s) having a number average molar mass ranging from 40,000 to 90,000 g/mol, relative to the total weight of the thickening composition.

According to one embodiment of the invention, the thickening composition according to the present invention comprises:
- from 10 to 90% by weight, preferably from 20 to 80% by weight, preferentially from 30 to 70% by weight, more preferentially from 40 to 60% by weight, of hydrocarbon oil(s) as previously defined here above; and
- from 10 to 90% by weight, preferably from 20 to 80% by weight, preferentially from 30 to 70% by weight, more preferentially from 40 to 60% by weight, of poly(farnesene) polymer(s) having a number average molar mass ranging from 40,000 to 90,000 g/mol, relative to the total weight of the thickening composition.

According to one embodiment of the invention, the thickening composition has a viscosity measured at 40° C. (measured for example according to the standard ISO 3104) ranging from 300 to 1000 mPa·s.

Thus, the thickening composition according to the invention will preferably comprise a single fatty phase.

The thickening composition according to the invention is preferably non-aqueous. In other words, the thickening composition according to the invention will preferably comprise less than 10% by weight of water, or even less than 5% by weight of water, ideally less than 1% by weight of water.

According to one embodiment of the invention, the thickening composition consists of one or more hydrocarbon oil(s) as defined here above and of one or more poly(farnesene) polymer(s) as defined here above.

Preparation of the Thickening Composition:

The thickening composition may be prepared by simply mixing the oil or oils derived from biological sources and the poly(farnesene) polymer, preferably at ambient temperature.

Additives:

The thickening composition according to the invention may also be mixed with any adjuvant or additive usually used in the field of interest considered, in particular in the cosmetics field. It is understood, that the person skilled in the art will exercise care in selecting the optional additive(s) of the composition according to the invention in such a manner as to ensure that the advantageous properties intrinsically attached to the thickening composition in accordance with the invention are not or substantially not altered by the potential addition envisaged.

Among the conventional adjuvants which may likely be contained (depending on the hydrosoluble or liposoluble nature of these adjuvants), mention may in particular be made of anionic foaming surfactants (such as sodium lauryl ether sulfate, sodium alkyl phosphate, sodium tridecyl ether sulfate), amphoteric surfactants (such as alkyl betaine, disodium cocoamphodiacetate) or non-ionic surfactants with an HLB greater than 10 (such as POE/PPG/POE, Alkylpolyglucoside, polyglyceryl-3hydroxylauryl ether); preservatives such as benzalkonium chloride; sequestering agents (EDTA); antioxidants; perfumes; dyestuffs/colouring agents such as soluble dyes, pigments and nacres; mattifying fillers, skin tensor/firming agent, whitening or exfoliating fillers; sunscreen filtres; cosmetic or dermatological active ingredients and agents that provide the effect of enhancing the cosmetic properties of the skin, whether hydrophilic or lipophilic; electrolytes. The quantities of these various adjuvants are those conventionally used in the field under consideration, for example from 0.01 to 20% of the total weight of the composition. By way of active ingredients that may be used in the thickening composition of the invention, mention may be made, for example, of hydrosoluble or liposoluble vitamins such as vitamin A (retinol or beta-carotene), vitamin E (tocopherol), vitamin C (ascorbic acid), vitamin B5 (panthenol), vitamin B3 (niacinamide), derivatives of these vitamins (in particular esters) and mixtures thereof; antiseptics; antibacterial active ingredients such as 2,4,4'-trichloro-2'-hydroxy diphenyl ether (or triclosan), 3,4,4'-trichlorocarbanilide (or triclocarban); anti-seborrheic; antimicrobials such as benzoyl peroxide, niacin (vit. PP); slimming agents such as caffeine; optical brighteners, and any active ingredients suitable for the final intended purpose of the composition, and mixtures thereof.

The thickening composition may for example additionally comprise a polar agent, in particular in the event of the oil derived from biological sources being a hydrocarbon oil, i.e. an oil with low polarity. The polar agent may be selected from among triglycerides. Said polar agent may be added in an amount ranging from 1 to 30% content by weight, or from 5 to 25% by weight, relative to the total weight of the thickening composition.

According to another embodiment, the thickening composition of the invention does not comprise triglycerides or comprises triglycerides in an amount of less than 0.01% by weight, relative to the total weight of the thickening composition.

According to another embodiment, the thickening composition of the invention does not comprise a polar agent or comprises polar agents in an amount of less than 0.01% by weight, relative to the total weight of the thickening composition.

According to one preferred embodiment, the thickening composition of the invention is essentially derived from bio-based sources, in other words, it preferably comprises at least 90% by weight, preferably at least 95% by weight, more preferably at least 98% by weight, or indeed even at least 99% by weight, of ingredients derived from biological sources, relative to the total weight of the thickening composition.

According to one embodiment of the invention, the thickening composition according to the invention has a refractive index of at least 1.445, preferably of at least 1.450, measured for example at 25° C. according to standard ASTM D 1218.

The present invention also relates to the use of the thickening composition according to the invention in cosmetic compositions, in particular as a thickening agent, sensory agent, film-forming agent, texturing agent, water resistance enhancing ("waterproofness") agent, moisturising/hydrating agent, conditioner, viscous oil, or agent that provides a second skin effect or indeed even as a gloss enhancing agent, or as an anti-pollution agent.

Cosmetic Composition:

The object of the present invention also relates to a cosmetic composition comprising the thickening composition according to the invention and:
- at least one fatty substance selected from among: plant oils that are different from those of the thickening composition, where appropriate, plant butters, ethers and fatty alcohols, oily esters, alkanes and silicone oils, preferably from oily esters, and/or
- at least one additive selected from among the aforementioned additives, preferably from anionic foaming surfactants (such as sodium lauryl ether sulfate, sodium alkyl phosphate, sodium tridecyl ether sulfate), amphoteric surfactants (such as alkyl betaine, disodium cocoamphodiacetate) or non-ionic surfactants with an HLB greater than 10 (such as POE/PPG/POE, Alkylpolyglucoside, polyglyceryl-3hydroxylauryl ether).

The fatty substance is preferably selected from among fatty substances exhibiting a low polarity.

Examples of plant oils include in particular oils of: wheat germ, sunflower, grape seed, sesame, corn, apricot, castor, shea, avocado, olive, soybean, sweet almond, palm, rapeseed, cottonseed, hazelnut, macadamia, jojoba, alfalfa, poppy, pumpkin, sesame, squash, rapeseed, blackcurrant, evening primrose, millet, barley, quinoa, rye, safflower seed, candlenut, passion flower, rose hip, or camellia.

Plant butters are fatty substances that have the same properties as plant oils. The difference between the two lies in the fact that butters are in solid form at ambient temperature. Also, unlike plant oils, the raw material from which a butter is extracted (pulp, seeds or almonds) is heated after having been ground for the extraction of the fat. Like plant oils, butters may be refined in order to provide for better preservation, neutralise odours, enhance the colour and the consistency thereof. Being nourishing and rich in antioxidants, the cosmetic properties of plant butters serve to improve the elasticity of the skin; protect against detrimental environmental elements by leaving a protective film on the epidermis, thereby reducing dehydration; and to repair and soothe the skin by regenerating the skin's natural hydrolipidic film. Examples of plant butters are in particular shea butter, cocoa butter, mango butter, shorea butter or even olive butter.

Fatty alcohols and ethers are long-chain, waxy fatty substances having remarkable properties in particular film-forming, emollient, moisturising, softening and protective properties. They act as moisturising oils and emulsifiers. Examples of fatty alcohols or ethers are: cetyl alcohol, stearyl alcohol, myristyl alcohol, lauryl alcohol, behenyl alcohol, cetearyl alcohol, dicaprylyl ethers, stearyl ethers, or octyldodecanol (identified by their International Nomenclature Cosmetic Ingredient (INCI) names).

Oily esters or esterified oils are the product of a reaction between fatty acids (longer chains acids, such as for example stearic acid, oleic acid, palmitic acid) and alcohols (fatty alcohols or polyols such as glycerol). These oils can contain substances deriving from petrochemicals, as is the case with Isopropyl Palmitate. Examples of oily esters are caprylic capric triglyceride, coco caprylate caprate, oleyl erucate, oleyl linoleate, decyl oleate, or even PPG-3 benzyl ether myristate (identified by their INCI names).

The term "silicone oils or polysiloxanes" is understood to refer to an oil comprising at least one silicon atom, and in particular at least one Si—O group. By way of silicone oil, mention may in particular be made of phenylpropyldimethylsiloxysilicate, dimethicones or else cyclopentasiloxane (identified by their INCI names).

This cosmetic composition comprises a physiologically acceptable medium, that is to say one which does not exhibit any deleterious side effects and in particular which does not produce unacceptable effects such as redness, flare-ups, tightness or stinging sensations for the user. This medium optionally comprises water and/or at least one oil as fatty substance, in addition to the aforementioned thickening composition.

According to one embodiment, the cosmetic composition has a content of thickening composition as described here above ranging from 1 to 80%, preferably from 5 to 70%, and advantageously from 10 to 50% by weight relative to the total weight of the composition.

According to one embodiment, the cosmetic composition has a content of thickening composition as described here above ranging from 1 to 50% by weight, preferably from 2 to 40% by weight, and advantageously from 3 to 30% by weight, relative to the total weight of the composition.

Thus, the cosmetic composition according to the invention may comprise from 0.1 to 15% by weight of poly(farnesene), preferably from 0.5 to 10% by weight of poly(farnesene), and advantageously from 1 to 5% by weight of poly(farnesene), relative to the total weight of the cosmetic composition, said poly(farnesene) preferably having a number average molar mass ranging from 20,000 to 90,000 g/mol.

The cosmetic composition according to the invention may thus be an anhydrous composition, an emulsion such as a water-in-oil (W/O) emulsion, an oil-in-water (O/W) emulsion, or a multiple emulsion (in particular W/0/W or O/W/O), a nano-emulsion, or even a dispersion, depending on the additives optionally introduced, and/or depending on an aqueous phase optionally introduced.

The cosmetic composition according to the invention may constitute, for example, a lip care composition, such as lip gloss or moisturising sticks for the lips, a mask composition, a repairing balm composition, a scrub and/or exfoliating composition intended for the face as well as for the hands (when it contains exfoliating particles), a makeup composition, a shaving composition, an aftershave balm composition, a scented composition, a composition for wipes, a makeup-removal composition or cleansing composition for the skin, and lips, a sunscreen composition (protection against UV), or after-sun composition, a skin massage composition, a composition for shower (care) balm, an antiperspirant composition.

The composition according to the invention may be a sunscreen composition for topical application, comprising (i) at least one sunscreen filter, such as an anti-UVA and/or an anti-UVB filter, and (ii) at least one thickening composition according to the invention, preferably in an amount ranging from 1 to 50%, preferably from 2 to 40%, and advantageously from 3 to 30% by weight relative to the total weight of the sunscreen composition.

The composition of the invention is advantageously characterized in that it exhibits a stability for a duration greater than or equal to 4 weeks, advantageously greater than or equal to 6 weeks, the stability being assessed after storing without agitation at ambient temperature, at 40° C., and at 50° C., and corresponding to a visual assessment of colour and appearance as well as an olfactory assessment, and/or a measurement of viscosity.

Use of the Thickening Composition:

The object of the invention also relates to the cosmetic use of the composition as defined here above for topical application, on the skin, the lips or the skin appendages (including the nails, the scalp, and the hair).

The object of the invention also relates to the cosmetic use of the cosmetic composition as defined here above as a skin care product (serums, creams, balms, etc), as a hygiene product, as a sunscreen/post sun product, as a makeup product, as a makeup removal product, as a scented product, as an antiperspirant product, as a lip care product, such as a lip gloss or moisturising sticks for the lips.

The thickening composition according to the invention provides the means to obtain an enhanced perception of the colour of the cosmetic composition that contains it, which makes it possible to reduce the amount of pigment used in said cosmetic composition.

The cosmetic composition according to the invention exhibits improved hydration or moisturising properties, as well as anti-pollution properties and enhanced gloss.

The thickening composition according to the invention and the cosmetic composition according to the invention may most particularly be used for topical application, in particular as a care product for the skin or the hair, as a makeup product, as a hair product, as a makeup removal product, as a scented product, as a sunscreen product, as a lip care product, such as a lip gloss or moisturising sticks for the lips.

The object of the invention indeed also relates to a cosmetic treatment process for treating the skin, lips or skin appendages, comprising at least one application step of applying to the skin, lips and/or skin appendages of a composition as defined here above.

The composition of the invention may also be used for the formulation of cosmetic compositions comprising other components or phases other than those described here above. It may in particular be the formulation of care-, hygiene-, or make-up compositions.

Cosmetic Treatment Process:

Finally, the invention also covers a cosmetic treatment process comprising at least one application step of applying, preferably by spreading, on the skin, lips or skin appendages, of the compositions according to the invention.

EXAMPLES

In the remainder of the present description, examples are given by way of illustration of the present invention and are in no way intended to limit the scope thereof.

Example 1: Preparation of the Thickening Compositions

The poly(farnesene) used in Examples 1 to 5 is completely hydrogenated and functionalised with hydroxyl groups. It has a number average molar mass of 71,000 g/mol.

It was prepared according to the operational method described in the patent document WO2018/052709.

Table 1 groups together the physicochemical properties of the hydrocarbon oil used in the examples.

TABLE 1

| Characteristics | Hydrocarbon oil |
|---|---|
| Aromatics (ppm) | <20 |
| Sulfur (ppm) | 0.11 |
| % iso paraffins (w/w) | 96.2 |
| % n-paraffins (w/w) | 3.8 |
| % naphthenic compounds (w/w) | 0 |
| C13 (iso) | 0 |
| C14 (iso) | 0 |
| C15 (iso) | 0 |
| C16 (iso) | 1.58 |
| C17 (iso) | 14.17 |
| C18 (iso) | 79.69 |
| C19 (iso) | 0.12 |
| C20 (iso) | 0.38 |
| C27 (iso) | 0.29 |
| Quantity of carbons of biological origin (%) | >98 |
| Initial boiling point (° C.) | 293.6 |
| Boiling point 5% (° C.) | 296.7 |
| Boiling point 50% (° C.) | 298.5 |
| Boiling point 95% (° C.) | 305.3 |
| Final boiling point (° C.) | 324.1 |
| Biodegradability-OECD (28 days) (%) | 83 |
| Refractive index at 25° C. | 1.4394 |
| Density at 15° C. (kg/m3) | 787.2 |
| Flash point (° C.) | 149 |
| Kinematic viscosity at 40° C. (cSt) | 3.87 |
| Vapour pressure at 20° C. (kPa) | <0.01 |
| Aniline point (° C.) | 93.2 |

Table 1: Physicochemical properties of hydrocarbon oil

The following standards and methods were used to measure the above properties:

flash point: EN ISO 2719 density at 15° C.: EN ISO 1185 viscosity at 4000: EN ISO 3104 aniline point: EN ISO 2977

Boiling point: ASTM D86
biodegradability: OECD 306 method
refractive index at 2000: ASTM D 1218
vapour pressure: calculated according to methods well known to the person skilled in the art.

The thickening compositions tested are set out in Table 2 here below. The percentages are percentages by weight relative to the total weight of the thickening composition.

TABLE 2

Thickening compositions

| | Composition 1 | Composition 2 | Composition 3 | Composition 4 |
|---|---|---|---|---|
| Hydrocarbon oil | 40% | 20% | 60% | 30% |
| Poly(farnesene) | 60% | 60% | 40% | 30% |
| Triglycerides | 0 | 20% | 0 | 40% |

Example 2: Evaluation of the Miscibility of the Thickening Composition with Fatty Substances The fatty substances tested are:
a plant oil: meadowfoam seed oil (according to the INCI name) having a density at 20° C. of 0.91 and comprising:
58.0-64.0% by weight of gadoleic acid (C20:1)
10.0-14.0% by weight of erucic acid (C22:1 d13)
3.0-6.0% by weight of docosenoic acid (C22:1 d5)
15.0-21.0% by weight of docosadienoic acid (C22:2)
relative to the total weight of the plant oil.
A plant wax: jojoba oil.

An oily ester: isononyl isononanoate (according to the INCI name), commercially available.
A silicone oil: cyclopentasiloxane (according to the INCI name), available commercially.
Squalane (according to the INCI name).

The manipulation consists in observing the miscibility of the thickening composition (Compositions 1 and 2 prepared in Example 1) with the fatty substances, by proceeding to add the fatty substance to be tested into the thickening composition by increasing weight percentage: 10%, 25%, 50%, 75% and 90%. These manipulations are carried out continuously. Observation of the mixing occurs between successive instances of addition. The addition is carried out in the same container.

The experiments are carried out on a quantity of thickening composition starting at a baseline of 45 g and finishing at 450 g. In fact, the additions are done as such on the base of 45 g present in the beaker:
10%: addition of 5 g of fatty substance to be tested.
25%: addition of 10 g of fatty substance to be tested in the mixture obtained previously $$((5+10)/(45+5+10)=0.25).$$

50%: addition of 30 g of fatty substance to be tested in the mixture obtained previously.
75%: addition of 90 g of fatty substance to be tested in the mixture obtained previously.
90%: addition of 270 g of fatty substance to be tested in the mixture obtained previously.

The final mixtures are stored in glass jars and observed on D+1. A mixture is said to be immiscible when sediments are visually observed.

The thickening composition according to the invention is miscible with silicone oil, when the silicone oil is present in an amount ranging up to 50% by weight.

The thickening composition according to the invention is miscible with the other fatty substances tested, when the fatty substance is present in an amount ranging up to 90% by weight.

Example 3: Sensory Analysis of Cosmetic Compositions Comprising the Thickening Composition According to the Invention Four cosmetic compositions were prepared and tested. The cosmetic compositions are described in Table 3 below. The percentages are percentages by weight relative to the total weight of the cosmetic composition.

TABLE 3

Cosmetic compositions

| | Placebo | Composition A | Composition B | Composition C | Composition D |
|---|---|---|---|---|---|
| Thickening composition 3 (from example 1) | 0 | 15% | 0 | 30% | 0 |
| Thickening composition 4 (from example 1) | 0 | 0 | 15% | 0 | 30% |
| DUB MCT 55/45 | 35% | 35% | 35% | 35% | 35% |
| DUB IPP | 35% | 35% | 35% | 35% | 35% |
| DUB ININ | 30% | 15% | 15% | 0 | 0 |

The compositions were evaluated, from the sensory and organoleptic standpoint, by a sensory panel made up of experts (5 persons).

The sensory and organoleptic analysis was carried out as follows:
Depositing of a drop of the product to be evaluated on the skin (underside of the forearm), by using a glass pipette.
Application of the product by using the fingers: evaluation of the appearance on the skin (gloss), of the feeling (sensory) on application, and of the final touch after application.

A rating score ranging from 0 to 3.5 is given for the two criteria: gloss on the skin, and the fat. The higher the rating, the better the sensation felt. The rating scores are shown in Table 4 below.

TABLE 4

| | Placebo | Composition A | Composition B | Composition C | Composition D |
|---|---|---|---|---|---|
| Sensory analysis of cosmetic compositions | | | | | |
| Gloss on the skin | 1.5 | 1.7 | 2.7 | 2 | 2.4 |
| Fat | 2.1 | 2.2 | 2.9 | 2.2 | 2.4 |

As illustrated in Table 4, the cosmetic compositions comprising a thickening composition according to the invention exhibit very satisfactory scores in terms of gloss on the skin and fat.

Example 4: Sensory Analysis of Cosmetic Compositions in the Form of Emulsions Comprising the Thickening Composition According to the Invention Three cosmetic compositions in emulsion form were prepared and tested. The composition of the emulsions is described in Table 5 below wherein the percentages are expressed as a percentage by weight relative to the total weight of the emulsion.

TABLE 5

Composition of emulsions with 5% and 10% thickening composition according to the invention

| Preparation phase | Trade Name | Ingredient | Placebo | Emulsion 10% | Emulsion 5% |
|---|---|---|---|---|---|
| A | SIMULSOL ® 165 | PEG-100 Stearate & Glyceryl Stearate | 3.50 | 3.50 | 3.50 |
| | MONTANOV ® 68 | CETEARYL ALCOHOL CETEARYL GLUCOSIDE 0.50 GLUCOSE AQUA | 1.50 | 1.50 | 1.50 |
| | TEGOALKANOL ® 1618 | CETEARYL ALCOHOL | 0.50 | 0.50 | 0.50 |
| | KARITE ® CP | BUTYROSPERMUM PARKII BUTTER | 2.00 | 2.00 | 2.00 |
| | DUB DSPE | Pentaerythrityl Distearate | 0.60 | 0.60 | 0.60 |
| | Thickening composition 3 or 4 | | 0 | 10.00 | 10.00 |
| | DUB ® ININ | Isononyl Isononanoate | 10.00 | 10.00 | 5.00 |
| B | DEMINERALISED WATER | AQUA | 74.15 | 64.15 | 69.15 |
| | CARBOPOL ULTREZ ® 21 | Acrylates/C10-30 Alkyl Acrylate Crosspolymer | 0.20 | 0.20 | 0.20 |
| | GLYCERINE CODEX | GLYCERIN | 3.00 | 3.00 | 3.00 |
| | RHODICARE ® T | XANTHAN GUM AQUA | 0.20 | 0.20 | 0.20 |
| C | PHENOXETOL | PHENOXYETHANOL | 0.80 | 0.80 | 0.80 |
| | CAUSTIC SODA SOLUTION A 10% | CAUSTIC SODA | 0.30 | 0.30 | 0.30 |
| D | DEMINERALISED WATER | AQUA | 2.00 | 2.00 | 2.00 |
| | HYDROLITE ®-5 | Pentylene Glycol | 1.00 | 1.00 | 1.00 |
| | CHLORPHENESIN ® BP73 | CHLORPHENESIN AQUA | 0.25 | 0.25 | 0.25 |

Each emulsion is prepared in the following manner:
Preparation of phase A by weighing the ingredients and placing the ingredients under agitation and heating at 75° C., until a homogeneous phase is obtained.
Preparation of phase B:
Weigh the water of phase B.
Without agitation, sprinkle on the Carbopol Ultrez 21 and leave to hydrate for 10 minutes without agitation.
Place under agitation and heat at 75° C. During the heating, with vigorous agitation, pour the premix of Rhodicare-t into the Glycerin.
Maintain under agitation until a homogeneous phase is obtained, while continuing to heat at 75° C.
At 75° C., under vigorous agitation, prepare the emulsion by pouring phase A into phase B.
Start the cooling while maintaining the speed of agitation. At 72° C. homogenise for 30 seconds with a Turrax® disperser set at 9500 rpm and continue the cooling under moderate agitation.
At 50° C., under agitation, successively introduce the ingredients of phase C and continue the cooling under moderate agitation.
At 30° C., under agitation, successively introduce the components of phase D.
Measure the pH and adjust it if necessary: 5.00<pH<6.00.
The compositions are evaluated, from a sensory and organoleptic standpoint, by a sensory panel made up of experts (5 persons).

The sensory and organoleptic analysis was carried out as follows:
Depositing of a drop of the product to be evaluated on the skin (underside of the forearm), by using a glass pipette, and analysis of the spreading of the drop.
Application of the product by using the fingers: evaluation of the spread and appearance on the skin (gloss).

A rating score ranging from 0 to 3.5 is given for the two criteria: gloss on the skin, and spreading. The higher the rating, the better the sensation felt. The rating scores are shown in Table 6 below.

TABLE 6

Sensory analysis of the emulsions according to the invention

|  | Placebo | 10% Emulsion with Thickening Composition 3 | 5% Emulsion with Thickening Composition 3 | 5% Emulsion with Thickening Composition 4 |
|---|---|---|---|---|
| Gloss on the skin | 0.4 | 0.9 | 0.5 | 0.8 |
| Spreading | 2.7 | 3.5 | 3.1 | 3.2 |

As illustrated in Table 6, the emulsions comprising a thickening composition according to the invention exhibit very satisfactory scores in terms of gloss on the skin and spreading.

Example 5: Determination of the Refractive Index

The refractive index of the thickening compositions 1 to 4 according to the invention (described in Table 2 above) was determined and compared to the refractive index of the hydrocarbon oil (described in Table 1 above).

The refractive index was measured at 25° C. according to the standard ASTM D 1218 and is indicated in Table 7 below.

TABLE 7

Refractive Index

|  | Composition 1 | Composition 2 | Composition 3 | Composition 4 | Hydrocarbon oil |
|---|---|---|---|---|---|
| Refractive index | 1.461 | 1.466 | 1.454 | 1.462 | 1.439 |

The refractive index of a composition is an indicator of the gloss of said composition. Thus, the higher the refractive index of a composition, the glossier is the composition. As shown in Table 7, the thickening compositions according to the invention exhibit a high refractive index, which proves that the thickening compositions according to the invention have very high gloss.

Example 6: Preparation of Other Thickening Compositions

The poly(farnesene) used in the remaining examples is fully hydrogenated and not functionalised with hydroxyl groups. It has a number average molar mass of 71,000 g/mol. It was prepared according to the operational method described in the patent document WO2018/052709, with the exception of the introduction of a functional group.

The oil derived from biological sources used in the remainder of the examples is the hydrocarbon oil described in Example 1.

The thickening compositions tested are set out in Table 8 below. The percentages are percentages by weight relative to the total weight of the thickening composition.

TABLE 8

|  | Composition 5 | Composition 6 |
|---|---|---|
| Hydrocarbon oil | 40% | 60% |
| Poly(farnesene) | 60% | 40% |

Example 7: Make-Up or Sunscreen Products

In this example, the properties of water resistance (waterproofness) and the colour pigment dispersing properties of compositions intended for makeup or sunscreen applications were evaluated.

The compositions evaluated are described in Table 9 below. The percentages are percentages by weight relative to the total weight of the composition.

TABLE 9

| Trade Name | Ingredient | Ex 7.1 | Ex 7.2 | Ex 7.3 | Ex 7.4 | Ex 7.5 | Ex 7.6 |
|---|---|---|---|---|---|---|---|
| A | Thickening composition 5 (example 6) | 42.5 | | | 10 | | |
| | Thickening composition 6 (example 6) | | 42.5 | | | | |
| PANALANE H-300E | Hydrogenated Polyisobutene | | | 42.5 | | 10 | |
| XIAMETER PMX 1502-FLUID | C11-13 isoparaffin and dimethiconol & Isohexadecane & Dimethicone | | | | | | 10 |
| EMOGREEN L19 | C15-19 alkane | 8 | 8 | 8 | 28 | 28 | 28 |
| BENTONE GEL VS-5PC V | Cyclopentasiloxane & Disteardimonium Hectorite & Propylene Carbonate | 30 | 30 | 30 | | | |
| BENTONE GEL IHD V | Isohexadecane & Disteardimonium Hectorite & Propylene carbonate | | | | 30 | 30 | 30 |
| B CREASPERSE GERANIUM (CPO63) | Hydrogenated Polydecene & Red 7 Lake (CI 15850) & Poly-Hydroxystearic Acid | 15 | 15 | 15 | | | |
| CREASPERSE WHITE R (CPO78) | Titanium Dioxide & Hydrogenated Polydecene and Hydroxystearic Acid | 3 | 3 | 3 | | | |
| KAHLWAX 8104 BEESWAX WHITE | Cera Alba | | | | 12 | 12 | 12 |
| CARNAUBA WAX SP-63 | Copernicia Cerifera (Carnauba) Wax | | | | 6 | 6 | 6 |
| CUTINA GMS V | Glyceryl Stearate | | | | 3 | 3 | 3 |
| C RED FRUIT FML00100 | Fragrance | 1.5 | 1.5 | 1.5 | | | |
| UNIPURE BLACK LC 989 HLC | CI 7749 9 & Hydrogenated Lecithin | | | | 10 | 10 | 10 |
| LEXGARD GMCY | Glyceryl Caprylate | | | | 1 | 1 | 1 |

The compositions Ex7.1, Ex7.2 and Ex7.3 are evaluated in terms of colour pigment dispersing properties by colorimetric analysis, according to the CMC acceptability system. As illustrated in Table 10 below, the compositions Ex7.1 and Ex7.2 according to the invention exhibit a more stable colour (see the value of dE-CMC) than the comparative composition Ex7.3.

TABLE 10

| | L* | a* | b* | C* | h | dE-CMC(l:c) |
|---|---|---|---|---|---|---|
| Ex7.1 | 34.1 | 50.26 | 15.57 | 52.61 | 17.21 | 0.65 |
| Ex7.2 | 34.02 | 49.75 | 15.38 | 52.07 | 17.18 | 0.52 |
| Ex7.3 | 33.8 | 49.69 | 14.63 | 51.8 | 16.41 | — |

The thickening composition according to the invention makes it possible to have good colorimetric properties, in particular for maintaining the colour, which enables it to be used satisfactorily in makeup compositions, for example.

It should also be noted that a more saturated/more intense colour is observed for Ex7.1 and Ex7.2 (criterion C). This enhances the colour perception, which could make it possible to reduce the content level of pigment used in the cosmetic composition.

The compositions Ex7.4, Ex7.5, Ex7.6 are evaluated in terms of water resistance through a clinical trial on 11 volunteer participants. Each composition is applied on the eyelashes of each volunteer, then left to dry for 5 minutes before exposing the face to steam (from a Vapozone) for 10 minutes.

Rating scores from 0 to 4 are assigned by professionals based on the traces of smudging of the composition after 10 minutes of exposure to steam. The scores are assigned as follows:
  4 if no smudging,
  3 if very slight smudging,
  2 if slight smudging,
  1 if medium smudging,
  0 if significant smudging.
A percentage of remanence is calculated from the average of the scores attributed as follows: % remanence=average of the scores/4*100. This percentage quantifies the water resistance.

It was observed that the composition according to the invention Ex7.4 exhibits a far greater water resistance than the comparative compositions Ex7.5 and Ex7.6. Indeed, the composition Ex7.4 exhibits more than 75% remanence while the compositions Ex7.5 and Ex7.6 exhibit only about 45% and about 52% remanence, respectively.

The thickening composition according to the invention provides the means to improve the water resistance properties of compositions, such as cosmetic compositions or sun protection compositions.

Example 8: Hair Products

In this example, the sensory properties of compositions intended for hair applications were evaluated.

The compositions evaluated are described in Table 11 below. The percentages are percentages by weight relative to the total weight of the composition.

TABLE 11

|   | Trade Name | Ingredient | Ex 8.1 | Ex 8.2 | Ex 8.3 |
|---|---|---|---|---|---|
| A | VARISOFT ® BTMS | | 8 | 8 | 8 |
|   | CUTINA ® PES | | 2 | 2 | 2 |
|   | KARITE ® CP | BUTYROSPERMUM PARKII BUTTER | 10 | 10 | 10 |
|   | EMOSMART ® L19 | | 5 | 5 | 5 |
|   | | Thickening Composition 5 (example 6) | 5 | | |
|   | | Thickening Composition 6 (example 6) | | 5 | |
|   | XIAMETER PMX 1503 FLUID | | | | 5 |
| B | DEMINERALISED WATER | AQUA | 62.82 | 62.82 | 62.82 |
|   | GLYCERINE CODEX | GLYCERIN | 3 | 3 | 3 |
| C | CHLORPHENESIN ® BP73 | CHLORPHENESIN AQUA | 0.28 | 0.28 | 0.28 |
| D | PHENOXETOL | PHENOXYETHANOL | 0.9 | 0.9 | 0.9 |
|   | ISOPENTYLDIOL | | 3 | 3 | 3 |

The compositions Ex8.1, Ex8.2, Ex.8.3 are evaluated in terms of suppleness, gloss, sensation of nourished hair through a clinical trial on 3 volunteer participants. Each composition is applied to the hair of each volunteer, and then left to dry.

Rating scores ranging from 1 to 5 are given for each criterion: supple softness of the hair after drying and feeling of nourished hair. The higher the rating scores, the better the property.

The rating scores are indicated in Table 12 below.

TABLE 12

|   | Ex 8.1 | Ex 8.2 | Ex 8.3 |
|---|---|---|---|
| Supple softness of the hair after drying | 2.8 | 2.8 | 2.3 |
| Feeling of nourished hair | 3.0 | 3.6 | 2.6 |

The thickening composition according to the invention provides the means to improve the nourishing properties of a hair composition, such as a hair mask.

Example 9: Skin Care Compositions

In this example, the film-forming properties that induce a moisturising effect and the anti-pollution properties of the thickening compositions according to the invention were evaluated.

The compositions evaluated are described in Table 13 below. The percentages are percentages by weight relative to the total weight of the composition.

TABLE 13

| Preparation Phase | INCI or Composition of the Invention | Ex 9.1 | Ex 9.2 | Ex 9.3 |
|---|---|---|---|---|
| A | Steareth-2 | 3 | 3 | |
|   | Cetyl Alcohol & Glyceryl Stearate & Peg-75 Stearate & Ceteth-20 & Steareth 20 | | | 5 |
|   | Steareth-21 | 2 | 2 | |
|   | PPG-15 Stearyl Ether | 2 | 2 | |
|   | Cetearyl Alcohol | 1.5 | 1.5 | |
|   | BUTYROSPERMUM PARKII BUTTER | 1 | 1 | |
|   | C10-18 Triglycerides | 2 | 2 | 4 |
|   | Glycol Palmitate & Glycol & Palmitic Acid | | | 4.5 |
|   | Theobroma Cacao Seed Butter | | | 2 |
|   | Macadamia Integrifolia Seed Oil | 1.5 | 1.5 | |
|   | C15-19 Alkane | 2 | 2 | 7 |
|   | Thickening Composition 5 (example 6) | 5 | | 5 |
|   | Dimethicone (Xiameter PMX-200 SIL FLUID 1000CTS) | | 5 | |
| B | AQUA | 72.8525 | 72.8525 | 65.25 |
|   | Disodium EDTA | | | 0.1 |
|   | GLYCERIN | 3 | 3 | 4 |
|   | Acrylates/C10-30 Alkyl Acrylate Crosspolymer | 0.25 | 0.25 | 0.2 |
|   | Xanthan Gum | | | 0.15 |
|   | Pentylene Glycol | | | 1 |
|   | Chlorphenesin | | | 0.2 |

TABLE 13-continued

| Preparation | | Content in % by Weight | | |
|---|---|---|---|---|
| Phase | INCI or Composition of the Invention | Ex 9.1 | Ex 9.2 | Ex 9.3 |
| C | PHENOXYETHANOL | 0.8 | 0.8 | |
| | AQUA and Sodium Hydroxide | 0.5475 | 0.5475 | 0.45 |
| D | AQUA | 1 | 1 | |
| | Phenoxyethanol | | | 0.8 |
| | Pentylene Glycol | 1 | 1 | |
| | CHLORPHENESIN | 0.25 | 0.25 | |
| E | Perfume | 0.3 | 0.3 | 0.35 |

The film-forming properties were evaluated by evaluating the Insensible Water Loss (IWL) over a duration of 2 hours (ie "Transepidermal Water Loss" or TEWL as per accepted terminology), during a clinical trial on 11 volunteer participants. The Insensible Water Loss (IWL) is the most commonly used measurement to quantify skin/external environment exchanges. This measurement makes it possible to evaluate the quantity of water evaporated through the skin, it is expressed in grammes per hour and per m² of cutaneous surface. The measurement is carried out by means of a Tewameter TM300 probe (Courage & Khazaka GmbH).

This study consisted in measuring the rate of IWL prior to the application (T0) and 2 hours (T2h) after application of the composition to the hands, over a zone to be treated and over a control zone.

The composition is applied over a zone measuring 16 cm² at a dosage of 2 mg/cm² on the zone to be treated and a control zone (not coated with the composition) measuring 16 cm² is also delimited.

Table 14 below summarises the IWL rates (average over the 11 volunteer participants) in g/m²/h at T0 and at T2h between the treated zone and the control zone for each of the two compositions tested (Ex9.1 and Ex9.2). The percentage of variation between T0 and T2h is also shown in Table 14.

TABLE 14

| | T0 | | T2h | |
|---|---|---|---|---|
| | Treated Zone | Control Zone | Treated Zone | Control Zone |
| Average IWL (g/m²/h)-Ex9.1 | 12.9 | 12.3 | 10.7 | 12.7 |
| Variation-Ex9.1 | 5.2% | | −15.9% | |
| Average IWL (g/m²/h)-Ex9.2 | 8.7 | 8.8 | 5.8 | 6.7 |
| Variation (%)-Ex9.2 | −1.1% | | −14.5% | |

The results show a reduction in water loss of almost 16% thanks to the composition Ex9.1 according to the invention. In comparison, the composition outside the invention Ex9.2 (dimethicone) provides a reduction in water loss of 14.5%.

The significant reduction in the loss of water thanks to the thickening composition according to the invention shows a film-forming effect and therefore an improvement in the moisturising properties thanks to the thickening composition according to the invention.

The anti-pollution properties of the composition Ex9.3 comprising the thickening composition according to the invention (described in Table 13) were evaluated by determining the effectiveness of the composition in limiting the deposits of carbon microparticles (air pollution model). The evaluation was carried out by image analysis on standardised photos acquired using the video-dermoscope C-Cube, by means of a clinical trial on 10 volunteer participants according to the following protocol:

Delimitation of 2 zones measuring 16 cm² (zone to be treated and control zone) on the forearms;

Application of 50 μL of an alcoholic dilution of synthetic sebum at 15% concentration to the predefined zones;

Application of the composition Ex9.3 at a dosage of 2 mg/cm² over the zone to be treated;

Depositing of 50 μL of a hydro-alcoholic suspension of 1.2% carbon particles on the predefined zones;

Acquisition of image (T0) by using the video dermoscope C-Cube;

Standardised wiping of the 2 zones by using a damp cotton square or disc, and then air drying;

Acquisition of image (T1) by using the video dermoscope C-Cube.

Table 15 below presents the number of dark pixels detected before the wiping (T0) and after the wiping (T1) of the control zone and the zone to be treated. The percentage of variation between the control zone and the zone to be treated is also indicated.

TABLE 15

| | T0 | | T1 | |
|---|---|---|---|---|
| | Treated Zone | Control Zone | Treated Zone | Control Zone |
| Zone (number of dark pixels detected)-Ex9.3 | 1426288 | 435687 | 1045398 | 4851 |
| Change (%)-Ex9.3 | −69.45% | | −99.54% | |

The percentage variation shows that the cosmetic composition according to the invention has anti-pollution properties since it makes possible a reduction of more than 99% of the pixels representative of carbon particles, and therefore of atmospheric pollution.

The invention claimed is:

1. A thickening composition intended for topical application on the skin, lips or skin appendages, said thickening composition comprising:
    at least one oil derived from a biological source, and
    at least one poly(farnesene) polymer having a number average molar mass ranging from 10,000 to 120,000 g/mol, said poly(farnesene) polymer being partially or fully hydrogenated and/or functionalised with hydroxyl groups,
    wherein the at least one oil derived from a biological source is a hydrocarbon oil comprising, based on the total weight of the hydrocarbon oil, greater than or equal to 90% by weight of isoparaffinic compounds.

2. The thickening composition according to claim 1, wherein the oil derived from a biological source is selected from among hydrocarbon oils, plant or animal oils in the form of acids, esters or amides, and mixtures thereof.

3. The thickening composition according to claim 1, wherein the oil derived from a biological source is a hydrocarbon oil.

4. The thickening composition according to claim 3, wherein the hydrocarbon oil is selected from among non-cyclic isoparaffins comprising from 14 to 18 carbon atoms.

5. The thickening composition according to claim 3, wherein the hydrocarbon oil comprises:
- a content by weight of isoparaffins, ranging from 95 to 100% relative to the total weight of the hydrocarbon oil; and/or
- a content of carbon derived from biological sources that is greater than or equal to 95%; and/or
- a content by weight of normal paraffins that is less than or equal to 10, relative to the total weight of the hydrocarbon oil; and/or
- a content by weight of naphthenic compounds that is less than or equal to 1%, relative to the total weight of the hydrocarbon oil; and/or
- a content by weight of aromatic compounds that is less than or equal to 500 ppm, relative to the total weight of the hydrocarbon oil.

6. The thickening composition according to claim 3, wherein the hydrocarbon oil is obtained by a method of catalytic hydrogenation at a temperature of 80 to 180° C., and at a pressure of 50 to 160 bars of a deoxygenated and/or isomerised biologically-sourced feedstock.

7. The thickening composition according to claim 1, wherein the poly(farnesene) polymer has a number average molar mass ranging from 20,000 to 90,000 g/mol.

8. The thickening composition according to claim 1, comprising, relative to the total weight of the thickening composition:
- from 10 to 90% by weight of oil(s) derived from biological sources; and
- from 10 to 90% by weight of poly(farnesene) polymer(s).

9. The thickening composition according to claim 1, that is selected from a thickening agent, sensory agent, film-forming agent, texturing agent, water resistance enhancing agent, moisturising/hydrating agent, conditioner, viscous oil, or agent that provides a second skin effect, in a cosmetic composition.

10. A cosmetic composition for topical cosmetic application on the skin, lips or skin appendages, said cosmetic composition comprising at least one thickening composition according to claim 1.

11. The cosmetic composition according to claim 10, comprising at least one fatty substance selected from among: plant oils, where appropriate other than the plant oils of said thickening composition, hydrocarbon oils, where appropriate other than the hydrocarbon oil of said thickening composition; plant butters; fatty ethers and fatty alcohols; oily esters; alkanes and silicone oils; and/or at least one additive.

12. The cosmetic composition according to claim 10 that is selected from a care product for the skin or the hair, a makeup product, a hair product, a makeup removal product, a perfumed product, a sunscreen product, a lip care product.

13. A cosmetic treatment process for the cosmetic treatment of the skin, lips or skin appendages, comprising at least one step of applying the thickening composition according to claim 1 or a cosmetic composition for topical application on the skin, the lips or skin appendages comprising the thickening composition.

14. A sunscreen composition for topical application, said sunscreen composition comprising (i) at least one sunscreen filter, and (ii) at least one thickening composition according to claim 1.

15. The thickening composition according to claim 3, wherein the hydrocarbon oil comprises a content by weight of isoparaffins ranging from 90 to 100%, a content by weight of normal paraffins ranging from 0 to 10%, relative to the total weight of the hydrocarbon oil.

16. The cosmetic composition according to claim 10, wherein the cosmetic composition comprises the at least one thickening composition in an amount ranging from 1 to 80% by weight relative to the total weight of the cosmetic composition.

17. The cosmetic treatment process according to claim 13, wherein the thickening composition 1 or the cosmetic composition are applied by spreading on the skin, the lips or skin appendages.

18. The sunscreen composition according to claim 14, wherein the at least one thickening composition represents from 1 to 80% by weight relative to the total weight of the sunscreen composition.

\* \* \* \* \*